(12) United States Patent  
Kumar et al.

(10) Patent No.: US 8,915,121 B2  
(45) Date of Patent: Dec. 23, 2014

(54) ENCAPSULATED DEVICE WITH INTEGRATED GAS PERMEATION SENSOR

(75) Inventors: Ramadas Senthil Kumar, Singapore (SG); Adrian Paul Burden, Malvern (GB); Soo Jin Chua, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 1241 days.

(21) Appl. No.: 12/521,427

(22) PCT Filed: Dec. 28, 2006

(86) PCT No.: PCT/SG2006/000408  
§ 371 (c)(1),  
(2), (4) Date: Aug. 4, 2010

(87) PCT Pub. No.: WO2008/082362  
PCT Pub. Date: Jul. 10, 2008

(65) Prior Publication Data  
US 2010/0294024 A1 Nov. 25, 2010

(51) Int. Cl.  
*G01N 7/00* (2006.01)  
*H01L 27/32* (2006.01)  
(Continued)

(52) U.S. Cl.  
CPC .......... *G01N 27/121* (2013.01); *H01L 51/5259* (2013.01); *H01L 27/3225* (2013.01);  
(Continued)

(58) Field of Classification Search  
CPC ................. G01N 27/048; G01N 2291/02845; G01N 27/12; G01N 27/121; H01L 23/564; H01L 23/26; H01L 51/5237; H01L 2924/12044; G01M 3/40; G01M 3/186; B82Y 30/00

USPC ................... 73/29.01, 29.02, 335.05, 335.02, 73/335.03, 335.06, 335.11, 29.05, 31.03, 73/52, 49.3, 865.8, 865.9  
See application file for complete search history.

(56) References Cited

U.S. PATENT DOCUMENTS 3,548,633 A 12/1970 Webb  
3,906,426 A 9/1975 Frazee et al.  
(Continued)

FOREIGN PATENT DOCUMENTS

DE 10208767 C1 7/2003  
JP 11-194107 A 7/1999  
(Continued)

OTHER PUBLICATIONS

Mattox, D.M. (1998). Handbook of Physical Vapor Deposition (PVD) Processing. (pp. 157-162). William Andrew Publishing/Noyes.*

(Continued)

*Primary Examiner* — Daniel S Larkin  
*Assistant Examiner* — Jamar Ray  
(74) *Attorney, Agent, or Firm* — Blakely, Sokoloff, Taylor & Zafman LLP (57) ABSTRACT

An encapsulated device comprising an integrated gas permeation sensor is provided, comprising a base substrate with an electronic component arranged thereon being enclosed within an encapsulation for protecting the electronic component from moisture and/or oxygen; at least one sensor is arranged within the encapsulation to measure the permeation of gas into the encapsulation; each sensor comprises an electrically conductive sensing element comprising a moisture and/or oxygen sensitive material, wherein the reaction of said material with moisture and/or oxygen results in a change in the electrical resistance/conductivity of the sensor.

20 Claims, 7 Drawing Sheets

(51) Int. Cl.
  *B82Y 30/00* (2011.01)
  *G01N 27/12* (2006.01)
  *B82Y 20/00* (2011.01)
  G01N 19/00 (2006.01)
  H01L 51/52 (2006.01)

(52) U.S. Cl.
  CPC ............ *B82Y 30/00* (2013.01); *H01L 51/5237* (2013.01); *H01L 27/3281* (2013.01); *H01L 2251/5369* (2013.01); *B82Y 20/00* (2013.01)
  USPC ....................... 73/31.03; 73/29.01; 73/335.02

(56) References Cited

U.S. PATENT DOCUMENTS

| | | | |
|---|---|---|---|
| 3,943,557 | A | 3/1976 | Frazee et al. |
| 4,057,823 | A | 11/1977 | Burkhardt et al. |
| 4,224,565 | A * | 9/1980 | Sosniak et al. ................ 324/694 |
| 5,606,264 | A | 2/1997 | Licari et al. |
| 5,837,935 | A * | 11/1998 | Carper et al. ............. 174/50.51 |
| 6,465,953 | B1 * | 10/2002 | Duggal ......................... 313/553 |
| 6,818,479 | B2 | 11/2004 | Boroson et al. |
| 6,866,901 | B2 | 3/2005 | Burrows et al. |
| 7,343,080 | B2 | 3/2008 | Gally et al. |
| 7,739,900 | B2 | 6/2010 | Reinert et al. |
| 2005/0168138 | A1 | 8/2005 | Okunaka et al. |
| 2005/0184661 | A1 | 8/2005 | Chiu et al. |
| 2006/0067645 | A1 | 3/2006 | Gally et al. |
| 2008/0141759 | A1 | 6/2008 | Reinert et al. |
| 2010/0089636 | A1 * | 4/2010 | Ramadas et al. .............. 174/521 |

FOREIGN PATENT DOCUMENTS

| | | | |
|---|---|---|---|
| JP | 11-306927 | A | 11/1999 |
| JP | 2000-315446 | A | 11/2000 |
| JP | 2001-264237 | A | 9/2001 |
| JP | 2003-157970 | A | 5/2003 |
| JP | 2004-037180 | A | 2/2004 |
| JP | 2005-190779 | A | 7/2005 |
| JP | 2006-241938 | A | 9/2006 |
| JP | 2008-518793 | A | 6/2008 |
| JP | 2008-523597 | A | 7/2008 |
| WO | WO 03/047317 | A1 | 6/2003 |
| WO | WO 2005/095924 | A1 | 10/2005 |

OTHER PUBLICATIONS

OLED at IMRE, Institute of Materials Research and Engineering, Apr. 2006, p. 7.*
International Search Report and Written Opinion mailed Feb. 22, 2007 in PCT/SG2006/000408, 13 pages.
International Preliminary Report on Patentability completed Nov. 7, 2008 in PCT/SG2006/000408, 3 pages.
Office Action for Japanese Counterpart Application No. 2009-543989, 4 pages, (Jul. 17, 2012).

* cited by examiner

ENCAPSULATED DEVICE WITH INTEGRATED GAS PERMEATION SENSOR

CROSS-REFERENCE TO RELATED APPLICATIONS

This application is a National Stage application of PCT/SG2006/000408, filed Dec. 28, 2006.

The present invention relates generally to the field of encapsulated devices, and more particularly to encapsulated devices with integrated sensors.

BACKGROUND OF THE INVENTION

Many electronic devices, such as organic light emitting devices (OLEDs), charged coupled devices (CCDs), and thin-film transistors (TFTs), organic Thin-Film Transistors (TFT), solar cells, comprise active components which are susceptible to degradation from exposure to moisture, oxygen and other gases found in the atmosphere. In order to ensure the longevity of these devices, some form of hermetic packaging is typically used to protect these devices from exposure to degradative substances.

As hermeticity is important for the operation of such devices, hermetic seal testing has become a vital part of the manufacture of these devices. For example, in the semiconductor industry, standard reliability qualification testing includes one or more humidity evaluations in which a sample quantity of devices are subjected to a humid environment and other conditions of elevated temperature, bias, and/or pressure.

A variety of hermeticity tests have been developed to evaluate the hermeticity of encapsulation packages. For example, for detecting fine leaks in integrated circuit (IC) packages, a mixture of helium gas with dry nitrogen, is sealed into the package, and a mass spectrometer is used to detect helium leaking from the package.

While the helium leak test method has been used on many types of semiconductor packages, it suffers from certain problems. Firstly, the helium leak test is generally only applicable for testing packages with cavities, and are not suitable for devices which do not comprise cavities, such as optoelectronic devices, MEMS or any other thin film microelectronic devices. Secondly, helium tends to separate from atmospheric nitrogen present in the device, due to differences in atomic weight, thus migrating to the top of the encapsulation cavity, affecting the thermal conductivity of components in the device as well as the index of refraction of the encapsulation, thereby yielding inaccurate results.

Another method that is currently employed to assess the condition of an electronic component within an encapsulation is direct observation of the optical properties of the electronic component. In OLEDs for example, observation of degradation patterns under the microscope can be carried out to assess the aging of the OLED. However, visual inspection methods are simplistic in nature and can provide only qualitative information about the encapsulated device, but is of limited use for accurate quantitative studies. In a factory line where tests are carried out on large numbers of newly fabricated OLEDs, visual inspection would be highly time consuming as well. Visual inspection is furthermore also not feasible once the OLED is integrated into a display panel.

In the past, some attempts have been made to integrate gas permeation sensors into encapsulation packages. U.S. Pat. No. 3,943,557 describes a semiconductor package with a hermeticity detector integrated into the semiconductor package. The hermeticity detector comprises a set of interdigitated electrodes that are spaced apart by a layer of cobalt oxide. In the absence of moisture, no current passes between the interdigitated electrodes. In the presence of moisture, however, the resistivity of the cobalt oxide reduces significantly, thereby shorting the interdigitated electrodes to trigger an alarm to indicate the ingression of moisture.

German Patent Application Publication No. DE 102 08 767 describes a measuring device for determining the permeability of a material that is used to form an encapsulation. The measuring device comprises a layer of corrosion sensitive material present in the encapsulation for electrical resistance measurements. As the corrosion-sensitive metal is degraded by oxygen/moisture entering the encapsulation, its electrical resistance increases. Moisture within the encapsulation is detected by monitoring the changes in electrical resistance in the corrosion sensitive element.

Despite these developments, limitations in integrated sensors in encapsulated packages still exist. In particular, the problem of sensors not having sufficient sensitivity to detect gas permeation at low levels of $10^{-4}$ g/m$^2$/day or better still remains. Continuing efforts are therefore needed to improve their reliability and accuracy.

Accordingly, an object of the present invention is to provide an encapsulated device having at least one gas permeation sensor enclosed within the encapsulation for measuring the permeation of gas into the encapsulation.

SUMMARY OF THE INVENTION

In a first aspect, the present invention is directed to an encapsulated device comprising a base substrate, an electronic component arranged on the base substrate and enclosed within an encapsulation that protects the electronic component from moisture and/or oxygen, and at least one gas permeation sensor arranged on the base substrate and enclosed within the encapsulation to measure the permeation of gas into the encapsulation. The at least one gas permeation sensor comprises an electrically conductive sensing element and an electrical connector capable of connecting the sensing element to a signal evaluation unit. The sensing element comprises a moisture and/or oxygen sensitive material, wherein the reaction of said material with moisture and/or oxygen results in a change in the electrical conductivity/resistance of the sensing element.

In a second aspect, the invention is directed to a method of fabricating the encapsulated device in accordance with the first aspect of the invention. The method comprises providing a base substrate for forming an electronic component thereon, forming an electronic component on the base substrate, forming on the base substrate at least one gas permeation sensor for monitoring the permeation of gas under vacuum, and forming an encapsulation over the electronic component and the sensor.

In a third aspect, the invention is directed to a system for fabricating an encapsulated device. The system comprises a vacuum chamber having arranged therein a holding jig arranged within the vacuum chamber for receiving a sample, a loadlock connected to the vacuum chamber, said loadlock being adapted to transport the sample onto the holding jig, a plasma source capable of dispensing plasma for cleaning the sample, at least a first material source adapted to form a gas permeation sensor on the sample and a second material source adapted to form an encapsulation over the sample, a linear motion drive capable of applying a normal force onto a sample on the holding jig, a heater coupled to the holding jig for heating a sample, and a UV source for curing a UV-curable polymer.

In a fourth aspect, the invention is directed to a method of determining the status of an electronic component arranged within the encapsulated device in accordance with the first aspect. The method comprises measuring the electrical conductivity of the sensor comprised in the encapsulation, determining from the electrical conductivity of sensor the amount of moisture and/or oxygen that has permeated into the encapsulation, and correlating the amount of moisture and/or oxygen that has permeated into the encapsulation to a status of the electronic component.

The invention is also directed to a system for determining the status of an electronic component in an encapsulated device, said system for determining the electrical conductivity/resistance of the sensor.

The present inventors have succeeded in integrating into any encapsulation a simple yet accurate gas permeation sensor comprising a sensing element that is reactive towards moisture and/or oxygen. As atmospheric gases permeate into the encapsulating, the sensing element comes into contact with ambient moisture and/or oxygen, and its electrical conductivity/resistance is progressively altered. By measuring this change in the electrical conductivity/resistance of the sensing element, it is possible to determine the amount of water and/or oxygen that has permeated into the encapsulation. Accordingly, the present invention can be used to facilitate both qualitative and quantitative evaluation of moisture and/or oxygen permeation in an encapsulated device. Due to the simple design of the sensor, the present invention is applicable to any existing encapsulated or packaged object.

The integration of a sensor into encapsulated devices, such as OLEDs, semiconductors and solar cells, provides practical benefits at the manufacturing level as well as at the end-user level. For example, the invention enables a user to estimate the remaining device operational life. At the production line, it enables quick checks to be carried out to determine whether fabricated devices have an intact encapsulation. The invention can also facilitate a study of the degradation mode of any encapsulated device in order to improve on the encapsulation fabrication technique.

In accordance with the first aspect of the invention, at least one gas permeation sensor is enclosed within the encapsulation to measure the permeation of gas into the encapsulation. The sensor comprises an electrically conductive sensing element comprising a material which reacts with moisture and/or oxygen such that its electrical conductivity or electrical resistance is changed as a result of the reaction. In a sense, the sensing element acts as a variable resistor whose resistance is altered through chemical reaction with moisture and/or oxygen. By measuring the change in the properties of the sensor, it is possible to infer from it the hermeticity of the encapsulation, as well as the operating status of the electrical component. For example, chemical reaction between a calcium sensing element in a sensor and water vapour causes some of the conductive calcium metal to be converted into non-conductive calcium hydroxide, thereby reducing the cross-sectional area through which electrical current is conducted through the sensing element. This results in an increase in electrical conductivity/resistance in the sensor, and this change is readily detected either by measuring the potential drop across the sensor or by measuring the resistance directly. An example of a gas permeation sensor that operates in such a manner is described in WO 2005/095924, for example.

The sensing element comprises a material that is reactive towards moisture and/or oxygen, such that it engages in a reaction with moisture and/or oxygen and becomes partially converted into a non-conductive material, and thereby altering its electrical properties. The material preferably shows measurable change in electrical conductivity/resistance upon reacting with moisture and/or oxygen. In some embodiments, the sensing element comprises a water and/or oxygen sensitive material such as a conductive organic polymer, metal, metal alloy, metal oxide, and combinations thereof. Exemplary materials include Group II metals such as Ca and Mg, as well as transition metals such as Fe. Conductive organic polymers may also be used, including polyaniline, polypyrrole and polythiophene, polyacetylene, poly-p-phenylene, and polyvinylpyridine, thiophene-bipyridine copolymers, polypyridine, polybipyridine, and organometallic polyphenylenes. Conductive metal oxides such as $VO_2$, $CrO_2$, $MoO_2$, $LiMn_2O_4$, $Cd_2SnO_4$, $CdIn_2O_4$, $Zn_2SnO_4$ and $ZnSnO_3$, and $Zn_2In_2O_5$ may be used as well.

The material of the sensing element may also be chosen based on the sensitivity of measurement that is desired. For example, if it is desired to obtain a sensitive measurement of moisture permeation into the encapsulation, a material having high reactivity towards moisture may be chosen. On the other hand, sensors for making measurements over a long period of time may comprise materials having a lower but measurable reactivity.

In one embodiment, the sensor is designed as an analogue to the electronic component whereby the rate at which the electronic component degrades within the encapsulation is matched by the rate at which the sensing element in the sensor degrades. The sensing element of the at least one sensor may have at least one physical or physico-chemical property that is at least substantially similar to the electronic component. For example, the surface area-to-volume ratio or the reactivity of the sensing element to moisture and/or oxygen may be substantially similar to the electronic component, or the dimension of the accessible surface of the sensor is similar to that of the electronic component. Another possible option of implementing this embodiment is to provide similar encapsulation structures around the gas permeation sensor and the electronic component, so that both sensor and electronic component are each exposed to the same rate of moisture and/or oxygen permeation.

Hermeticity of the encapsulation may be tested during the manufacturing process, or during use of the final product containing the encapsulated device. For the purpose of failure testing of individual encapsulated electronic components during the manufacturing process, for example, a single gas permeation sensor arranged near the electronic component may be sufficient to determine whether an encapsulation structure is airtight or not. For large OLED display units comprising many electronic components, it may be of interest to evaluate the hermeticity of the encapsulation of the entire display unit, so several tens or hundreds of gas permeation sensor may be integrated into the device to determine the exact location of a defect in the encapsulation. In consumer electronics products, it may also be of interest to the end user also to utilise a plurality of sensors to evaluate the condition of the electronic component, so that projections concerning the remaining operational life of the electronic component can be made.

A variety of arrangements of the sensor within the encapsulation have been contemplated. In principle, each gas permeation sensor may be placed at any available space within the encapsulation. For example, the sensor may be placed near the edge of the encapsulation to avoid having to alter the existing architecture of the electronic component. Alternatively, the sensor may be positioned close to the electronic device to assess more accurately the permeation conditions near the electronic device. In embodiments where a plurality of sensors are included, each sensor may be arranged around the electronic component, or for failure testing purposes, the sensors may be arranged at locations in the encapsulation at which the hermetic seal is suspected to be weak. The gas permeation sensor may also be arranged in a regular grid arrangement, interspersed throughout the encapsulation.

In applications in which the sensor is integrated into small electronic devices, the plurality of sensors may be designed to be sufficiently small and arranged to occupy any convenient location within the encapsulation without disrupting the architecture of the electronic component. In embodiments in which the sensors are integrated into OLEDs, the sensing element of the sensor may have a surface area that is exposed for contact with moisture/oxygen which is less than $0.5\ cm^2$, or less than $0.1\ cm^2$, the width of the sensing element being twice its length. Sensor size may also be designed to be equivalent to OLED pixel size. The distance between the sensor and the electronic component on the substrate may be between about 1 μm and 100 μm. The distance between sensor and electronic component may be between 1 μm and 10 μm if fabrication is carried out via precise fabrication techniques, such as lithography. On the other hand, a larger gap of 100 μm may be used when shadow mask is used to fabricate the sensor and device. Adjacent sensors may be spaced apart from each other at any suitable distance, e.g. at least about 1 cm.

In order to prevent any short-circuiting between circuit lines of the sensor and circuit lines of the electronic component due to the proximity of the sensor to the electronic component, an electrically insulating material may be interposed between the sensing element and the electronic component, for example. In one embodiment, the electrically insulating material is selected from polyimide, parylene, polystyrene and polyvinyl chloride.

Supplementary materials may be included in the sensor to improve its performance. For example, a liner layer comprising a polymer that is substantially permeable to gas may be applied onto one or both surfaces of the sensing element, to achieve uniform degradation of the sensing element. Such a polymer may be an organic polymer selected from the group consisting of acrylic polymers, and parylene type polymers, or an inorganic polymer comprising a silicone-based polymer. In another example, a protective layer covering at least a portion of the sensing element may also be introduced to protect the sensing element from physical damage during fabrication. The protective layer may comprise materials such as a metal, a metal alloy, a metal oxide, an organic polymer and combinations thereof.

The encapsulation for protecting the electronic component from moisture and/or oxygen may assume any suitable configuration or arrangement known in the art, such as barrier stack structures as described in or WO 03/047317, or rim-sealed structures as described in U.S. Pat. No. 6,81118,479, or multilayer thin-film configurations as described in U.S. Pat. No. 6,866,901 in which a barrier film is laid over the electronic component, thereby sandwiching the electronic component against the substrate, or any suitable combination of these encapsulation configurations.

Regardless of the encapsulation type being used, an electrical connector connected to the sensing element of the sensor extends through the encapsulation, so that they are exposed for contact with a driver circuit or a signal evaluation unit or any other external circuit. The electrical connector may comprise at least two electrodes. Electrodes may be in the form of metal contact lines, or a conductive film which extends through the encapsulation to be exposed for contact.

For certain applications requiring stringent barrier properties in conjunction with a flexible encapsulation, a multilayer thin-film encapsulation may be used. Multilayer thin-films typically comprise one or more layers of barrier material that has low moisture and/or oxygen permeability. These materials may be selected from the group consisting of metal oxides, ceramic oxides, inorganic polymers, organic polymers and mixtures and combinations thereof. Some examples of organic polymer barriers include epoxy polymers, polysulfide, silicone and polyurethane. Organic barrier layers include parylene, polyimide or acrylic based polymer hard coats without any nano-particles. Inorganic materials such as BaO, SrO, CaO and MgO materials can also be used. Additionally, the barrier layer materials can be selected from various metallic elements such as Ti, Mg, Ba, and Ca. The barrier layer can be deposited by either physical or chemical vapour depositions methods. The thickness of the barrier layer may typically range from 10 nm to 200 nm.

The inventors have found that the integration of a gas permeation sensor into an encapsulated device can be achieved with minimal compromise to the hermeticity of the encapsulation by implementing a multilayer thin film comprising at least one layer having distributed therein reactive nanoparticles capable of interacting with moisture and/or oxygen to retard the permeation of moisture and/or oxygen into the encapsulation. As used herein, the term "interacting" refers to any physical or chemical interaction between moisture and/or oxygen and the nanoparticles, so that moisture and oxygen are removed from the gas permeating the encapsulation, and thus prevented from reaching the electronic component. This definition includes interactions such as chemical reaction as well as physical adsorption of the water and/or oxygen molecules. For example, the nanoparticles may comprise a material capable of adsorbing water and/or oxygen, being a material such as zeolites, or carbon nanotubes. The nanoparticles may also comprise a material capable of reacting with water and/or oxygen. Examples of such materials include metals and metal oxides such as Ti, Mg, Ba, Ca, $Al_2O_3$, $TiO_2$, ZnO, SrO, CaO, MgO, and BaO. Inert nanoparticles, i.e. particles which do not react with moisture and/or oxygen, may also be included in the multilayer film in order to obstruct the permeation of moisture and/or oxygen into the encapsulation. Examples of materials which can be used to form inert nanoparticles include gold, copper, silver, platinum, silica, wollastonite, mullite, monmorillonite, silicate glass, fluorosilicate glass, fluoroborosilicate glass, aluminosilicate glass, calcium silicate glass, calcium aluminum silicate glass, calcium aluminum fluorosilicate glass, titanium carbide, zirconium carbide, zirconium nitride, silicon carbide, or silicon nitride, metal sulfides, and a mixture or combination thereof. The nanoparticles may be distributed within a polymer, or any other suitable binder for holding the nanoparticles.

In one exemplary embodiment, at least one barrier layer having low moisture and/or oxygen permeability, and at least one sealing layer comprising nanoparticles capable of interacting with moisture and/or oxygen are included in the multilayer film to improve the gas barrier properties of the encapsulation. Metal oxide barrier layers are conventionally known to provide strong gas barrier properties. However, pinhole defects are typically found in these metal oxide layers, limiting their gas barrier properties. The inventors have found that by using metal oxide barrier layers in combination with a layer of nanoparticles, the gas barrier property of the multilayer film is improved substantially, as the nanoparticles are thought to seal the defects in the metal oxide barrier layer. In some preferred embodiments, the barrier layer may comprise metal oxides such as $Al_2O_3$, $HfO_2$, $TiO_2$ or indium tin oxide (ITO), for example.

The concentration of nanoparticles in the sealing layer can be varied according to how stringent the barrier properties of the encapsulation are required to be. In theory, it should be advantageous to employ a high concentration of nanoparticles in order to increase the water and/or oxygen scavenging ability of the encapsulation. However, in display devices in which optical quality is important, such as OLED applications, requirements may be placed on the amount and size of nanoparticles to be included in the multilayer film. For example, in order to prevent light scattering through the multilayer film, the size of the nanoparticles is preferably smaller than the characteristic wavelength of the OLED. The characteristic wavelength is defined as the wavelength at which the peak intensity of OLED light spectrum occurs. When the encapsulation layer designed for TOLED or see-through displays, the size of the getter particles may be typically less than ½ and preferably less than ⅕ of the characteristic wavelength. Typically these ratios correspond to particle sizes of less than 200 nm and preferably less than 100 nm. In some encapsulation designs, larger particles may be desirable, for example where it is required to have scattering of the emitted light.

In one embodiment, the nanoparticles are rod-shaped and have a diameter of 30 to 50 nm and length of between 100 nm to 400 nm. It may be advantageous to use nanoparticles of different shapes and sizes in order to customise the random packing density of nanoparticles in the multilayer film to achieve effective sealing of the electronic component.

Where the electronic component comprises an OLED or any other component that emits light, any optical film known in the art may be included in the multilayer film to improve its optical properties. Optical films such as diffuser films may be provided to achieve optimum levels of light transmission while effectively diffusing the light. Optical films may be provided as a light extraction layer (in the case of top-emitting OLEDs). Traditional light diffusion films may comprise a PET base material with an acrylic or fixative surface coating. The optical film may also comprise an inorganic transparent oxide film. The optical film can be deposited by any suitable fabrication method, such as physical vapour deposition (sputtering, thermal evaporation or electron beam evaporation), plasma polymerization, CVD, printing, spinning or any conventional coating processes including tip or dip coating processes.

In order to further reduce the permeation of moisture and/or oxygen through the encapsulation and to provide additional mechanical protection for the encapsulated electronic device and integrated sensor, further encapsulation structures may be placed over the multilayer film. For example, a cover substrate may be arranged onto the multilayer film, interfaced by an adhesive layer tacking the cover substrate onto the multilayer film. It is also possible to include a cover substrate without the multilayer film in the case of a rim-sealed encapsulation structure, such that an inert gas filled space is defined within the encapsulation. The cover substrate may also be selected from either a hard or flexible but preferably scratch resistant material that can withstand impact forces and thus reduce physical damage to the multilayer film and/or the electronic component. Examples of materials that can be used include polyethylene (PET), polypropylene (PP), polycarbonate, glass, indium tin oxide, and transparent plastics.

The base substrate supporting the electronic component and the gas permeation sensor can comprise any durable material having gas barrier properties. The substrate supporting the electronic component and sensor may comprise a polymeric material, including organic polymers such as polycarbonate, polyethylene, polythersulfone, epoxy resins, polyethylene terephthalate, polystyrenes, polyurethanes and polyacrylates. It may also comprise inorganic polymers such as silicones, polydimethylsiloxanes, biscyclopentadienyl iron, polydichlorophosphazene and derivatives thereof.

Base substrates are optionally coated with barrier films comprising single or multiple transparent metal oxide layers serving as barrier layers. Metal oxide barrier films (also known as barrier stacks) normally comprise multiple alternating layers of organic and inorganic thin barrier films. Organic coatings, such as acrylics, normally are used as a sandwich layers between two consecutive barrier oxide films. The barrier stack substrates can be transparent or non-transparent and can be cut into preferred dimensions. In organic light emitting display (OLED) applications, exemplary barrier films are preferably substantially transparent.

An important consideration for integrating a gas permeation sensor into the encapsulation is the issue of integrating sensor drive circuitry into the architecture of the electronic component. In exemplary embodiments of the present invention, integration of the gas permeation sensor is achieved by providing separate circuit lines (independent of the circuit lines for the electronic component) for the sensor within the encapsulated device, so that the gas permeation sensor can be connected to an external circuit and operated independently of the electronic component. It is known also that both passive and active matrix OLEDs comprise column and row electrodes which may be tapped to drive currents through the sensor, from which gas permeation measurements may be made.

The segment drivers and common drivers of a conventional OLED driver, such as those provided by Solomon Systech Ltd., may be modified by incorporating circuitry to operate the gas permeation sensor. In this manner, the electronic component and the gas permeation sensor can be coupled to a common drive circuit. However, it is also possible for the electronic component and the gas permeation sensor to be connected to separate drive circuits, i.e. the gas permeation sensor is connected to a first drive circuit, and the electronic component is connected to a second drive circuit. For example, the drive circuit for the gas permeation sensor may comprise a system for determining the status of an electronic component in an encapsulated device in accordance with a further aspect of the invention as described below. Where a separate drive circuit is used for the gas permeation sensor, no modification needs to be made to the existing drive circuit for the electronic component.

In one embodiment, the electrical connectors of the gas permeation sensor may be coupled to a signal evaluation unit to measure a property associated with the electrical resistance of the sensor. Examples of a signal evaluation unit includes an ammeter, voltmeter, ohmmeter, multimeter, wattmeter, potentiometer, and source meter etc. A display unit capable of displaying a quantitative value associated with the amount of moisture and/or oxygen that has permeated through the base substrate, such as an LCD display, may be included in the signal evaluation unit. The gas permeation sensor may be arranged on the side of the base substrate that faces the enclosure in which the object to be protected is placed while the display unit is arranged on the external side of the base substrate in order to facilitate easily reading of the hermeticity measurements.

A feedback controller for modulating the power supplied to the electronic component may be coupled to a drive circuit connected to the gas permeation sensor or the signal evaluation unit measuring the change in the sensor so as to receive feedback on the extent of moisture and/or oxygen degradation within the encapsulation. The power supplied to the electronic component can be made to vary according to the feedback provided by the sensor. For example, luminescent devices such as OLEDs become dimmer over time due to the degradation of the active luminescent material. In order to compensate for the loss of brightness, more electrical power may be supplied to the OLED. Any suitable feedback control algorithm may be used in which the feedback controller increases the power that is being fed to the electronic component as the extent of gas permeation into the encapsulation increases, for example. A feedback control module may incorporated into the drive circuit of the gas permeation sensor. In order to provide the feedback to modulate the current supplied to the OLED via the column/row electrodes. Alternatively, a simpler solution would be to include a separate drive circuit to avoid having to rework existing integrated drivers.

The present invention is applicable to both rigid and flexible encapsulation structures used to encapsulate any article that may be damaged from exposure to moisture and/or oxygen. Although reference may be to the encapsulation of OLEDs, it is to be understood that the present invention is applicable for any encapsulated object or device, including electronic components, food items and pharmaceutical drugs. Some examples of electronic components include solar cells, passive and active Organic Light Emitting Devices (OLEDs), charged-coupled devices (CCDs), micro-electro-mechanical sensors (MEMS), and thin-film transistors (TFT).

Other than encapsulated electronic devices, the invention is also applicable to any hermetic packaging, including conventional packaging laminates, on which it is desired to integrate a gas permeation sensor, such as Tetra-Pak® packaging materials for food or blister packs and containers for pharmaceutical drugs. The gas permeation sensor can be readily integrated into any existing packaging material in order to provide hermeticity readings of the enclosure within the packaging. Accordingly, the invention is directed to a package for protecting an oxygen and/or moisture sensitive object. The package comprises a base substrate having low oxygen and/or moisture permeability, and at least one gas permeation sensor that is capable of measuring the permeation of gas through the base substrate arranged on the base substrate. Each of the gas permeation sensors comprises an electrically conductive sensing element comprising a moisture and/or oxygen sensitive material, wherein the reaction of said material with moisture and/or oxygen results in a change in the electrical resistance/conductivity of the sensing element. An electrical connector capable of connecting the sensing element to a signal evaluation unit is also provided.

It is contemplated that the package is useful for enclosing any object to be protected from moisture and/or oxygen, including electronic components, pharmaceutical drugs, food substances and chemicals. Therefore, the term "package" as used herein may refer to any packaging laminate that is arranged/folded to form an enclosure in which the oxygen and/or moisture sensitive object to be protected is arranged. It may also refer to a strip pack, blister package, pre-fillable syringe, medication tube, parenteral vial, ampul, prefillable inhaler, intravenous container, bottle, caps/closures, or a prescription container. The package may also refer to containers used to store hazardous substances, such as radioactive substances, poisonous chemicals, for example. The "base substrate" in this context refers to any part of the walls of the package.

The integration of the sensor into the encapsulated device is carried out in accordance with the method herein described as the second aspect of the invention. The method comprises forming an electronic component on a provided base substrate, and then forming the gas permeation sensor on the base substrate under vacuum conditions. An encapsulation is subsequently formed over the electronic component and the sensor, either in the presence of an inert gas or under vacuum conditions. "Vacuum conditions" herein refers to an environment in which atmospheric pressure is significantly lowered. Such conditions may range between conventional medium vacuum to ultra high vacuum. In some embodiments, the vacuum conditions of between about $10^{-3}$ to about $10^{-9}$ mbar, or about $10^{-6}$ to about $10^{-7}$ mbar, is used during the formation of the sensor and/or the encapsulation.

Prior to using the substrate, the surface of the base substrate may be cleaned, for example, by wet chemical cleaning and/or dry oxygen or argon plasma treatment. In one embodiment, the step of cleaning a surface of the substrate is carried out prior to forming the electronic component and the sensor onto the substrate. It has been found that removing surface contaminants on the substrate surface significantly improves the contact between the substrate and the encapsulation, leading to improved barrier properties. The surface of the substrate may be cleaned by wet chemical cleaning, or more preferably via dry argon or oxygen plasma treatment.

The sequence of forming the encapsulated device according to the invention can be carried out in a variety of ways depending on the encapsulation design, OLED architecture, substrates and also batch or roll to roll processes.

Due to the different requirements for forming each component of the encapsulated device, fabrication may be carried out over several stages. For example, the fabrication of the electronic component, such as an OLED, may be carried out in an evaporation chamber. As cleaning may be carried out in a plasma chamber, the cleaned substrate may be transferred under vacuum to the evaporation chamber. After forming the electronic component on the substrate, fabrication of the sensor may be carried out in a glove box. In order to maintain a contamination-free environment, transfer may also be carried out either under an inert atmosphere or under vacuum.

The sensor for monitoring the status of the electronic component may be formed by depositing two separate electrodes on the substrate, and depositing a sensing element between the two electrodes. After the sensor and the electronic component is formed, a primary encapsulation comprising a multilayer film for providing protection against moisture and oxygen may be formed over the electronic component and the sensor. The multilayer film may be formed by any chemical or physical deposition method. A cover may be further attached over the encapsulated device. An ultra-violet light curable adhesive can be coated over the sensor and the electronic component to allow for the attachment of a cover onto the encapsulated device. This may comprise the application of UV-curable adhesive, and subsequent exposure of the adhesive to ultra-violet light, thereby curing the adhesive.

The integrated sensor according to the present invention allows for real-time monitoring of the permeation of oxygen and moisture into the encapsulated device, from which the status of the electronic component within the encapsulation may be indirectly determined. In other words, the integrated sensor facilitates a method of determining the status of an electronic component in an encapsulated device. This method is useful carrying out failure analysis on a non-functional electronic component to determine whether a breached encapsulation is the cause for the failure of the electronic component, for example. Where a plurality of sensors are arranged in different portions of the encapsulation, the location of the defect in the encapsulation that gives rise to the failure can be readily detected. This helps to isolate causes of failure to certain steps in the fabrication process quicker, leading to a shorter turnaround time for failure analysis.

This method comprises measuring the electrical conductivity of the sensor enclosed in the encapsulation, determining from the electrical conductivity of the sensor the amount of moisture and/or oxygen that has permeated the encapsulation, and correlating the level of moisture and/or oxygen that has permeated the encapsulation to a status of the electronic component. The term "status" herein refers to the operational status of the electronic component, such as a particular condition in the electronic component that is indicative of failure. The status of the electronic component is determined indirectly by placing the sensor within the encapsulation containing the electronic component. As both sensor and electronic device are subjected to the same level of exposure to moisture and/or oxygen, the degradation of the sensor (via reaction with moisture and/or oxygen within the enclosure) can be correlated with the status of the electronic component, thereby making it possible to determine the status of the electronic component. For example, if it is known that the electronic component reaches critical failure condition after exposure to [y] grams of water vapour, and it can be determined that a sensor displays a change in electrical resistance of [z] Ohms after exposure to the same [y] grams of water vapour, then the critical failure level of the electrical component can be readily determined by measuring the electrical resistance of the sensor.

In one embodiment, electrical and/or physical evaluation of the encapsulated device is performed in addition to sensor determination of the status of the electronic component to determine whether the electronic component enclosed in the encapsulation is functional. The additional steps for evaluating the encapsulated device may be helpful especially in for embodiments in which the sensor determines the status of the electronic component indirectly, as indirect measurement provides there is no real indication of the functional status of the electronic component. Therefore, by measuring the actual properties of the electronic component, such as its electrical resistance or conductivity, may provide useful information on the actual condition of the electrical component. Physical evaluation may also be carried out by a trained technician, for example by observing whether there are obvious physical defects in the encapsulation leading to the failure of the device.

The integrated sensor can be used to carry out a variety of measurements, such as determining the remaining lifetime of the electronic component. In addition, measurements provided by the sensor provides data for evaluating the integrity of the encapsulation. This is useful, for example, as part of a testing system in the back-end stage of a manufacturing process for checking batches of fabricated encapsulated devices to determine whether encapsulated device is functional. In the case of display applications in consumer electronics, the sensor may be coupled to an integrated circuit with a programmed logic to display a warning signal, either on the encapsulated device or the system of which the encapsulated device is a part, when the level of moisture and/or oxygen that has permeated the encapsulation exceeds a threshold level. It may be then considered that the encapsulated device has deteriorated to the point that it is undependable for normal sustained service, for example.

In accordance with another aspect of the invention, a system for fabricating an encapsulated device with integrated gas permeation sensor in accordance with the first embodiment of the invention. The system comprises a vacuum chamber, a holding jig arranged within the vacuum chamber. The vacuum environment is used to carry out the fabrication of the gas permeation sensor. A first material source may be provided within the vacuum environment to form a gas permeation sensor on a sample base substrate, and a second material source may likewise be provided within the vacuum environment to form an encapsulation over the sensor and the electronic component. Alternatively, the fabrication of the electronic component or the encapsulation process may be carried out at separate stages outside of the vacuum chamber.

In one embodiment, the vacuum chamber comprises a plurality of serially connected sub-chambers for carrying out an in-line fabrication process. Due to space constraints imposed by the different equipment needed for carrying out each stage of the fabrication process, separate sub-chambers may be provided. For example, the first material source and the second material source may be each connected individual sub-chambers.

To facilitate transfers of a base substrate under vacuum or inert atmosphere from one chamber to another, a load lock system may be used. A conventional loadlock may be mounted to a gate valve attached to a main vacuum chamber. A substrate can then be easily moved into position through the large entry door onto the transfer stage in the loadlock chamber. After the loadlock is evacuated to the desired vacuum level, and the gate valve opened, the substrate is transferred into the process chamber through a magnet carriage along the main shaft of the loadlock. This allows repeated substrate loading and unloading without breaking vacuum in the main chamber. If vacuum chamber comprises a plurality of serially connected sub-chambers, the loadlock may comprise an extendable shaft movable through each individual sub-chamber.

High vacuum pumping outfits may be connected to the vacuum chamber, including mechanical booster, rotary, turbo, cryo-pumping stations which can deliver ultra high vacuum for the vacuum sealing applications. Additionally, pressure gauges, gas lines, pressure transducers and isolation valves may be included to monitor the vacuum in the vacuum chamber.

A holding jig for receiving a substrate holding table on which to form the encapsulated device is further provided. A substrate holding table (platform) may be attached to the holding jig, and may preferably includes a heating unit to provide heat of up to 100° C. or more, and a temperature controller for maintaining the required temperature. The heating process may be used to melt the adhesive while vacuum bonding the cover substrate and the device.

A linear motion drive is used to apply a normal force onto a sample on the holding jig, and may be used to compress a cover substrate onto an adhesive. The linear motion drive may be operated by a pneumatic actuator or with external motor with an axial load of about 5 lb to 100 lb or more to provide a pressure range of 40 to 80 psi for encapsulation.

In one embodiment, the system further comprises tracks for aligning the motion of the linear motion drive with respect to the holding jig. The linear motion drive and holding jig alignment may be directed along a supporting frame and linear ball guides. The supporting jig is designed such that the adhesive can be loaded onto the jig through load lock of the vacuum chamber. Similarly, the device or substrates can be transferred to the substrate holder through the load lock for the secondary sealing process.

Any conventional RF plasma cleaning source may be provided for carrying out surface pre-treatment. An example is the Evactron® plasma source from XEI Scientific, Inc. which uses air as oxygen source to produce oxygen radicals. In the context of the system, the plasma source may be adapted for external mounting on the vacuum chamber.

Other features which may be incorporated into the system include a substrate holding table with x, y & z axis controller for positioning the holding table, as well as a radio frequency power controller for controlling the RF power of the plasma source. A UV source may be included in the system to cure any UV-curable adhesive that is used in the encapsulation. Wavelengths of 365 nm & 300 nm with the respective intensities of 85 mW/cm$^2$ and 22 mW/cm$^2$ may be used to cure the adhesive.

In accordance with a further aspect of the invention, a measurement or evaluation system for determining the status of an electronic component in an encapsulated device is provided. Such a system comprises a signal evaluation unit adapted to couple to the sensor of an encapsulated device in accordance with the first aspect of the present invention. The signal evaluation unit is capable of measuring a property associated the change in electrical conductivity/resistance of the sensor. Examples of the signal evaluation unit include ammeter, voltmeter, ohmmeter, multimeter, wattmeter, and potentiometer. A display unit may be optionally provided to display a quantitative value associated with the permeation of gas into the encapsulation of the encapsulated device.

To automate the entire measurement process, the measurement system may comprise a drive circuit for operating the sensor to obtain readings therefrom, as well as a drive circuit for operating the electronic component in the encapsulated device. For example, the electronic component may be initially operated to check whether it is still functional; if the electronic component is not functional, a further test using the gas permeation sensor may be carried out to check whether the encapsulation is damaged. On the other, if the electronic component is still functional, then it may be concluded that the encapsulation is intact. The signal evaluation unit of the system may be comprised in the drive circuit that operates the electronic component, or it may be an independent device that is attached to only to the sensor.

These aspects of the invention will be more fully understood in view of the following description, drawings and non-limiting examples.

BRIEF DESCRIPTION OF THE DRAWINGS

Illustrative embodiments will now be described by way of non-limiting examples only, with reference to the accompanying drawings, in which.

DETAILED DESCRIPTION

Figure 1:
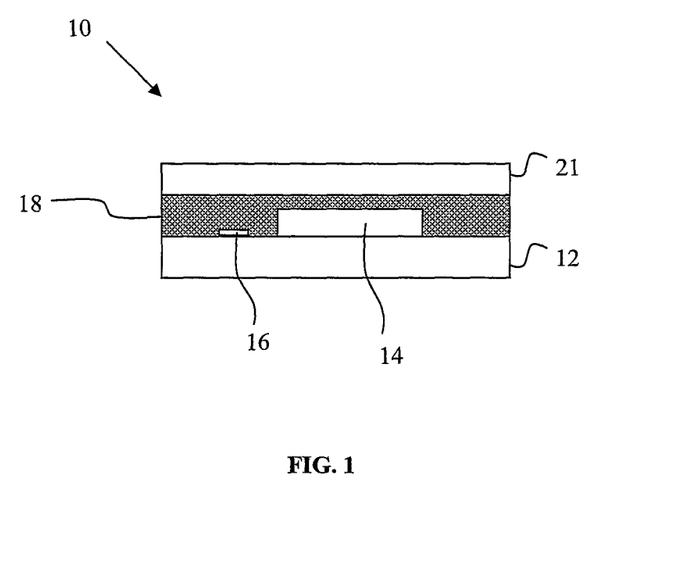
FIG. 1 shows a simplified diagram of an encapsulated device comprising an integrated sensor.

FIG. 1 shows a simplified schematic diagram of an encapsulated device 10 according to one embodiment of the invention. The device comprises a base substrate 12 which supports an OLED device 14 and a sensor 16 for determining the status of the OLED device 14. The sensor 16 is arranged alongside the OLED device 14 and both are encapsulated within an encapsulation 18. Both OLED device 14 and sensor 16 are powered by driver electronics with circuitry located on the base substrate. A cover 21 is attached over the encapsulation 18.

Figure 2:
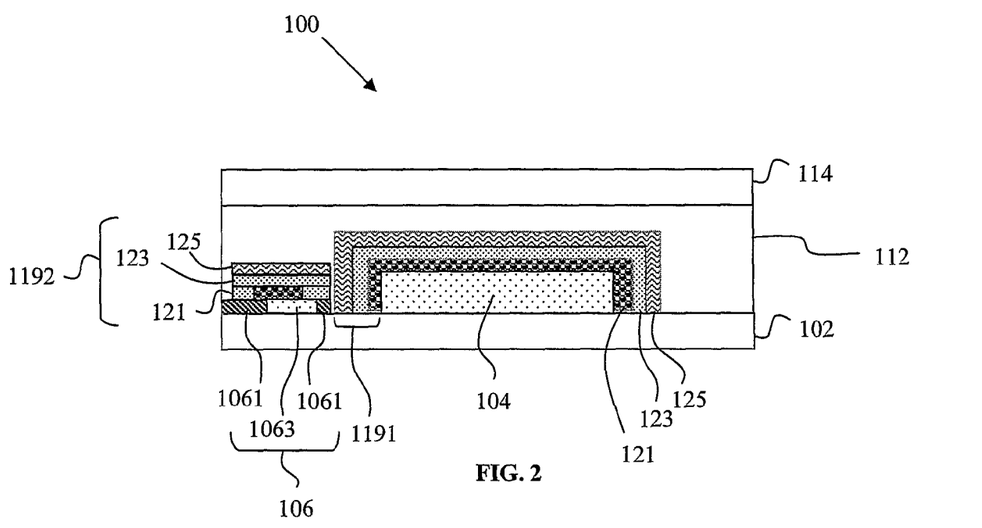
FIGS. 2 and 3 show exemplary embodiments of an encapsulated device according to the invention in which the encapsulation comprises a multilayer film having a layer of nanoparticles for removing moisture and/or oxygen.

FIG. 2 shows an encapsulated device 100 according to an exemplary embodiment of the invention. An OLED 104 and a sensor 106, comprising conductive tracks 1061 and a sensing element 1063, are arranged on a base substrate 102, each having an encapsulation comprising a multilayer film 1191, 1192 formed over their surface. The encapsulation further includes a barrier adhesive pad 112 in which the sensor 106 and the OLED 104 are embedded, so that a cover substrate 114 can be attached thereon, thereby sandwiching the OLED 104 and the sensor 106 between the base substrate 102 and the cover substrate 114. Multilayer films 1191, 1192 comprise an innermost nanoparticulate layer 121 comprising nanoparticles for interacting with moisture and oxygen. The next two layers above it are optical layers 123, 125 for improving the diffusion of light through the encapsulation.

Figure 3:
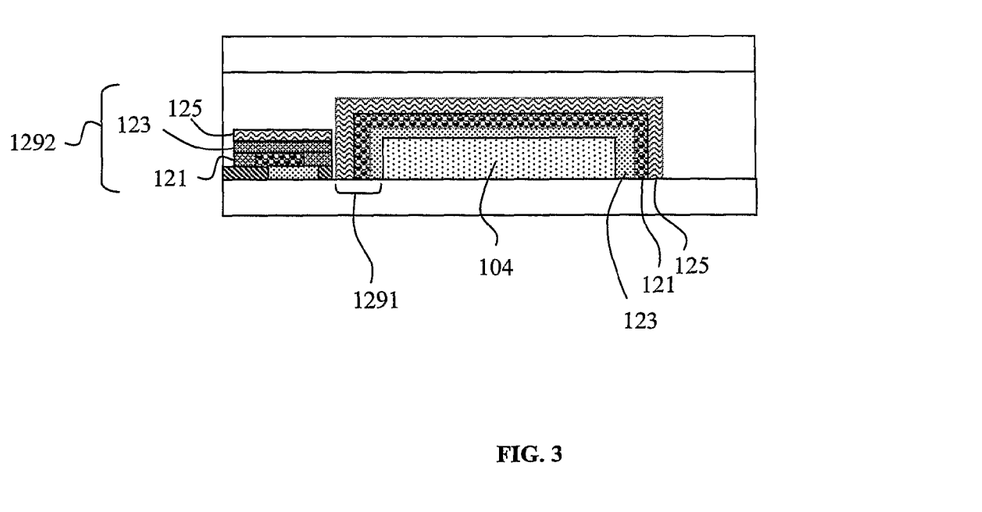

In the embodiment shown in FIG. 1, the arrangement of layers in the multilayer film 1191 covering the OLED 104 are identical to the multilayer film 1192 covering the sensor 106. However, the arrangement of layers may differ if desired. As shown in another exemplary embodiment depicted in FIG. 3, the multilayer film 1291 covering the OLED 104 comprises a first optical layer 123 as the innermost layer, followed by the nanoparticulate layer 121, and then a second optical layer 125.

Figure 4:
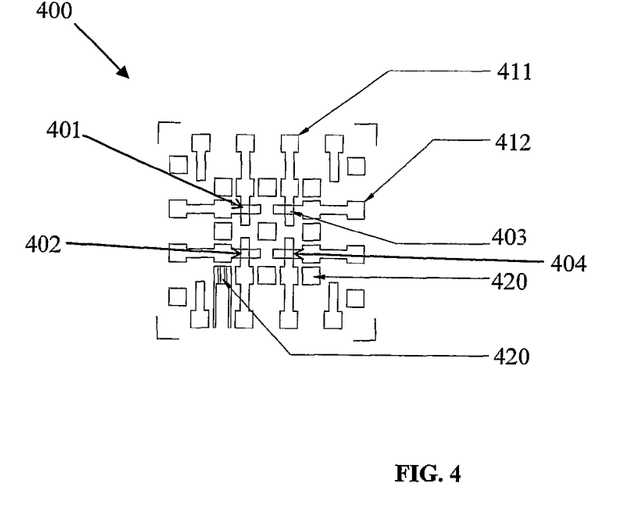
FIG. 4 depicts multiple sensors integrated within an encapsulated device with four OLEDs.

FIG. 4 shows an encapsulated device 400 comprising multiple sensors integrated within an OLED architecture comprising multiple OLEDs. The encapsulated device 400 comprises four OLEDs 401, 402, 403, 404 located at the junctions of anode lines 411 and cathode lines 412. Anode lines 411 and cathode lines 412 collectively make up the electrode lines of the device. Gas permeation sensors 420 are arranged in between electrode lines. In this embodiment, a total of nine sensors form a grid surrounding the four OLEDs. The grid of sensor, as opposed to a single sensor, can be used to detect precisely at which part of the device does moisture/oxygen enter the encapsulation.

Example 1

Fabrication of an OLED with Integrated Sensor

1. Surface Preparation of Substrates

Silicon oxide coated soda-lime glass substrates (display-quality glass) were cut into 50 mm×50 mm pieces and also any required sizes for use as a base or cover for the OLEDs. The pneumatically operated hollow die punch-cutting equipment or any conventional slitting machine could be used to slice the samples into the specified or required dimensions.

The water vapor permeation in the present encapsulation package may be mainly through the interface of the adhesive and substrate and also diffusion through adhesive sealing. The suitable surface pre-treatment process such as plasma treatment can eliminate the adhesion issues. Accordingly, they are rinsed with isopropyl alcohol (IPA) and blow-dried with nitrogen. These processes help to remove macro scale adsorbed particles on the surface. Acetone and methanol cleaning or rinsing is not recommended. After nitrogen blow-dry, the substrates are placed in the vacuum oven, with the pressure of $10^{-1}$ mbar, for degassing absorbed moisture or oxygen. The vacuum oven is equipped with fore line traps to prevent hydrocarbon oil back migrating from vacuum pump to the vacuum oven. Immediately after the degassing process, the barrier stacks are transferred to the plasma treatment chamber (e.g. ULVAC SOLCIET Cluster Tool). RF argon plasma is used to bombard the surface of the barrier film with low energy ions in order to remove surface contaminants. The base pressure in the chamber was maintained below $4\times10^{-6}$ mbar. The argon flow rate is 70 sccm. The RF power is set at 200 W and an optimal treatment time usually 5 to 8 eight minutes is used depending on the surface condition.

2. OLED Fabrication

The OLED architecture described in WO 03/047317 A1 has been adopted in the present example. ITO-coated glass with a sheet resistance of 20 Ω/square was used as a substrate for the OLED device fabrication. Wet chemical cleaning was undertaken with acetone and methanol and followed by dry oxygen plasma treatment. Poly (styrene sulfonate)-doped poly (3,4-ethylene dioxythiophene) (PEDOT) was used as a hole transport layer (HTL). The commercially available phenyl-substituted poly(p-phenylenevinylene) (PPV) yellow light emitting polymer was used. A 20 nm thick calcium film covered with a 200 nm thick silver cathode was deposited by thermal evaporation in an ULVAC cluster system at a base pressure of $2.0\times10^{-6}$ Torr. A silver film was used to protect the underlying calcium. Wet chemical cleaning was undertaken with acetone and methanol and followed by dry oxygen plasma treatment. 75 nm NPB is deposited in high vacuum $2\times10^{-6}$ Pa at 270° C. Small molecule based OLED structure was adopted in which 65 nm thick electroluminescence layer tris-(8-hydroxyquinoline) aluminum (AlQ3) is deposited at 270° C. under high vacuum of $2\times10^{-5}$ Pascal. A 5 Å thick LiF is deposited at 650° C. as an interlayer between EL and cathode. The cathode aluminium was deposited using thermal evaporation technique to the thickness of 200 nm.

3. Calcium Sensor Fabrication

After surface plasma treatment, the substrates are transferred under vacuum to an evaporation chamber, where a calcium sensor layer and the silver electrodes are deposited. The two silver electrodes has dimension 2 cm by 2 cm. The sensing element is fabricated in between the two electrodes and designed to be 1 cm long, 2 cm wide and 150 nm thick. The measured resistivity of the sensor element is 0.37 Ω-cm. After the deposition process, a load lock system is used to transfer the sample to a glove box under dry nitrogen at atmospheric pressure.

An UV (ultraviolet) curable epoxy is applied on to the rim of the OLED glass substrate followed by sealing with a 35 mm by 35 mm glass slide. A 400 W metal halide UV light source 2000-EC series UV light source (DYMAX Corporation) is used to cure the UV epoxy. Wavelengths of 365 nm and 300 nm with the respective intensities of 85 mW/cm$^2$ and 22 mW/cm$^2$ are used to cure the epoxy. The curing time was about 2 minutes. The test sample with its accompanying sensor is placed in a humidity chamber (WK1 Model, Weiss, Germany), which humidity and temperature can be set to any desired level. The electrodes of the sensor are connected to a constant current source meter (Keithley) and the measurement current is set constant at 1 mA to avoid any electro-chemical-induced reaction at the contacts. Lab view software is used to record the data when required.

After the plasma treatment process, the barrier stacks are transferred to a vacuum evaporation chamber (thermal evaporation) under vacuum where 150 nm calcium is deposited through a suitable mask into the space between the two transparent conductive oxide strips with a thickness of between 120 nm to 500 nm. After the calcium deposition, a 100 nm transparent or opaque insulating film is deposited to protect the calcium sensor. The insulating film could be any type of organic or inorganic films deposited by PVD or CVD processes. However, transparent lithium fluoride (LiF) or magnesium fluoride (MgF) is preferred as on of the embodiment. The encapsulated test cell is then transferred to a humidity chamber (WK1 Model, Weiss, Germany) and the rate of change of calcium resistance over time is monitored. Measurements could be done at different temperatures and relative humidity, all at atmospheric pressure conditions. The temperature is in the range from ambient to 95° C. conditions. The relative humidity can be up to 100% depending on humidity chamber specifications. The calcium test cell's conductive track terminals are connected to a constant current source (Keithley source meter), which is interfaced with a computer. Resistance of the calcium sensor/silver track is monitored every second and plotted automatically by the computer using lab view software. A Dynamic Signal Analyser with a FFT analysis is proposed to take the noise spectrum measurement automatically at periodic intervals of one second.

4. Multilayer Film Proximal Encapsulation

Nanoparticulate layers may be derived from a mixture of polymerisable acrylic acid containing a dispersion of nanoparticles, and which can be cured to forma nanostructure-surface after curing. Spin coating, screen printing or physical vapour deposition or chemical vapour deposition methods, can be used to deposit the mixture onto the OLED and sensor. HfO$_2$ UV filter layer and optical layers can also be deposited by PVD methods including sputtering, thermal evaporation or electron beam evaporation, plasma polymerisation, CVD, printing, spinning or any conventional coating processes including tip or dip coating.

5. Fabrication Equipment

Figure 5A:
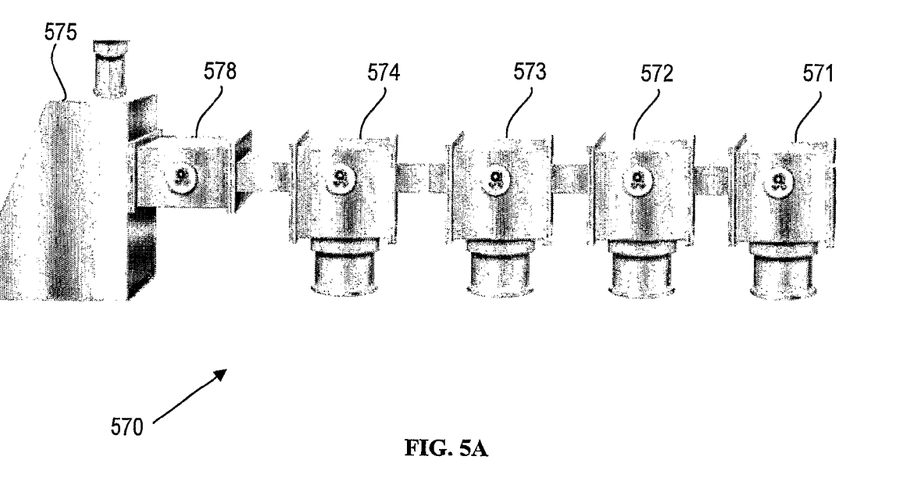
FIG. 5A shows an in-line fabrication system comprising a plurality of serially connected sub-chambers for fabricating an encapsulated device with a sensor.

The fabrication process described above may be carried out either in an in-line system or a roll-to-roll system. An in-line fabrication system 570 is depicted in FIG. 5A. The system comprises serially connected sub-chambers used for carrying out the steps of cleaning the base substrate, forming the electronic component, forming the gas permeation sensor, and then carrying out the encapsulation of the device, each step being carried out within separate sub-chambers. For instance, in the case of an OLED, the formation of OLED anode, organic EL layer, and cathode may be carried out in sub-chambers 571, 572 and 573, respectively, and gas permeation sensor is carried out in sub-chamber 574. Plasma cleaning and encapsulation may be carried out in a sub-chamber 575. The base substrate, carrying both sensor and electronic component, may finally be transported by a loadlock 578 into the sub-chamber 575, which may be a glove box, for example.

Figure 5B:
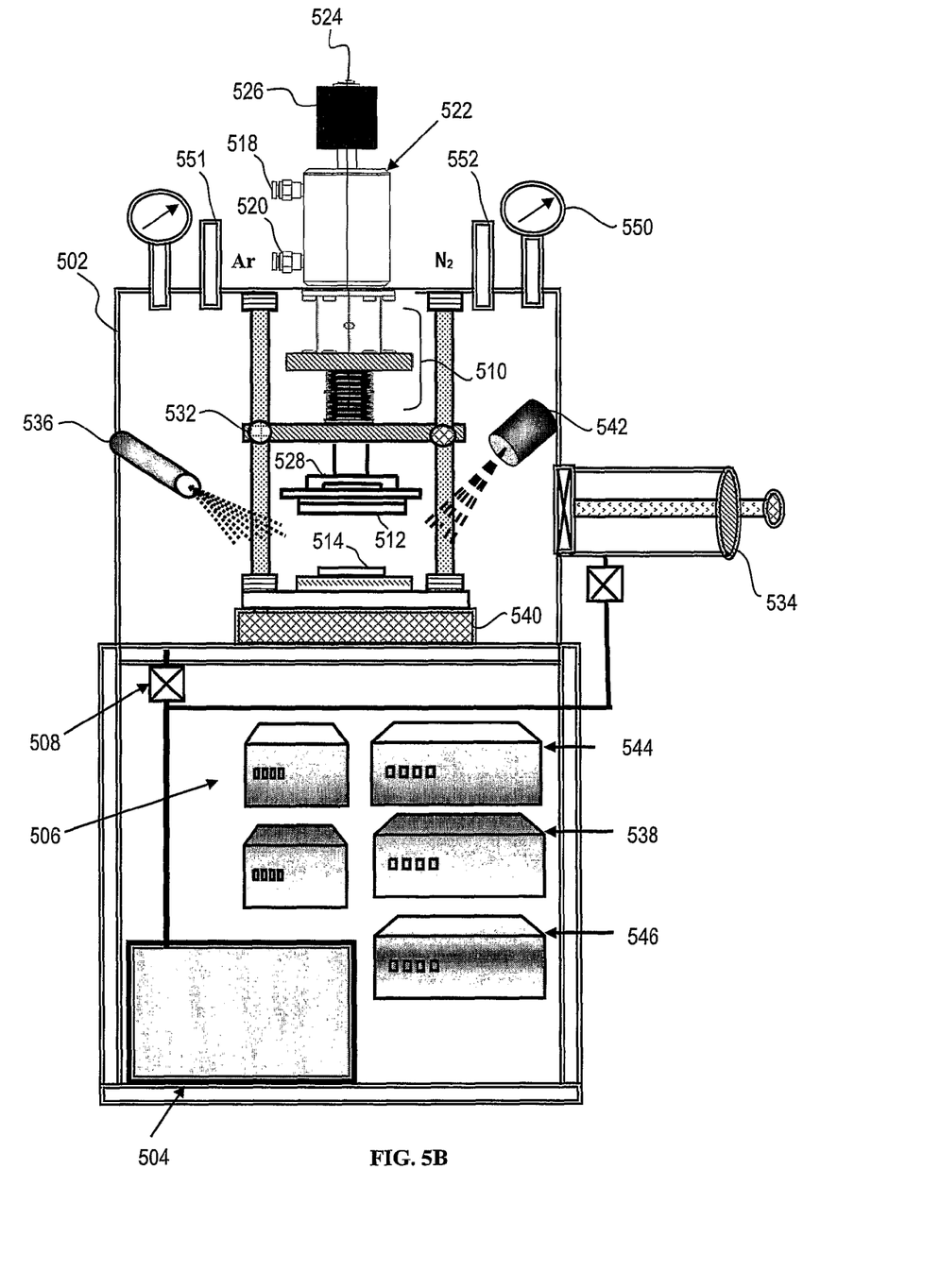
FIG. 5B shows details of a sub-chamber in which encapsulation is done.

In one exemplary embodiment, sub-chamber 575 may be a lab-scale glove box 500 for carrying out gas permeation sensor batch fabrication and encapsulation as shown in FIG. 5B. In this example, the vacuum chamber 502 has dimensions of 400 mm×500 mm×650 mm is connected to the high vacuum pumping station 504 (preferably mechanical booster with combination of rotary vacuum pump) and maintained at a base pressure $10^{-4}$ mbar. The high vacuum Pirani gauge 506 is used to monitor the vacuum pressure. The isolation valve 508 is used for isolating the vacuum pumping station 504 and the vacuum chamber 502. The linear motion drive 510 is used for sealing the adhesive pad 512 onto the OLED device 514 under vacuum. The linear motion drive 510 is mounted through a KF25 flange connection 516 to the vacuum chamber and it is pneumatically operated to drive the linear motion system.

Pneumatic linear motion feedthrough provides action for linear motion by applying a suitable compressed air pressure in the range of 40 to 80 psi. The compressed air is admitted through the inlet 518 and outlet 520 of the pneumatic actuator. Linear travel can be shortened or lengthened by turning the adjustment knob located at the top end of the pneumatic actuator 522. Once adjusted, the jam nut 524 locks the adjustment knob 526 in place. Linear travel adjustment can be made up to the required travel distance. A suitable adhesive holding jig 528 is connected to the linear motion drive 510 for holding the adhesive pad 512 used for sealing the device. The linear drive's axial load is typically 20 lb. The holding jig 528 is also used to apply pressure while the adhesive sealing process is undertaken. The pressure typically applied is in the range of 40 to 80 psi and the required pressure is tailored to the type of substrate/device used. The pressure can be applied either on the rim or the entire face of the substrate. The different types of holding jigs can be used as per the requirement of packaging. They are constructed of high grade vacuum compatible materials. The use of welded stainless steel bellows and linear bearing shaft support provide reliability and smooth operation. Pneumatic feedthroughs can be chosen from industry standard components, such as, either conflat compatible Del-Seal CF metal seal flanges or ISO KF Kwik-Flange elastomer seal port mounts.

The smooth operation of the linear motion drive, holding jig movements, and alignments with the substrates are carefully controlled by the supporting frame 530 and linear ball guides 532. The holding jig is designed such that the adhesive can be loaded onto the jig through a load-lock 534 of the vacuum chamber. Similarly, the device or substrate can be transferred to the substrate holder through of load-lock for the secondary sealing process.

The vacuum chamber 502 is further equipped with a plasma source 536 for surface pre-treatment or cleaning before the adhesive bonding process. The RF power controller 538 is used for controlling the RF power of the plasma source. Surface preparation consists of cleaning or surface modification done to the as-received sample or devices in order to obtain desired and reproducible properties. In the case of a polymer substrate, there are many avenues for surface contamination on the barrier film surface and also the polymer base substrate tends to absorb water vapor due to long storage time and from handling and exposure to ambient conditions. Any surface contamination would certainly affect adhesion of the adhesive pad. RF argon plasma is used to bombard the surface of the substrate or primary sealed device with low energy ions in order to remove surface contamination. The base pressure in the chamber is maintained below $4 \times 10^{-6}$ mbar and is monitored by a pressure monitor 550. The argon flow rate is 70 sccm. The RF power is set at 200 W and an optimal treatment time is normally 5 to 8 eight minutes depending on the surface condition. The argon gas line 551 is connected to the vacuum chamber to introduce argon used for plasma treatment. The nitrogen gas line 552 is connected to the vacuum chamber for venting the chamber after the plasma treatment process.

The substrate heating table 540 can provide up to 100° C. and the temperature controller is used to maintain required temperature. The heating process to melt the adhesive during vacuum bonding the device. After the vacuum sealing process, the adhesive can be cured by exposure to UV light for 30 seconds. A 400 W metal halide light UV source 542 (model 2000-EC) is used to cure the adhesive. Wavelengths of 365 nm & 300 nm with the respective intensities of 85 mW/cm$^2$ and 22 mW/cm$^2$ may be used to cure the adhesive.

Accordingly, the sequence of fabrication can be chosen flexibly according to the encapsulation design, OLED architecture, substrates and can be used not only for batch and in-line fabrication systems shown herein, but can also be adapted to roll-to-roll processes as well.

Example 2

Characterisation of Encapsulated Device

The following results demonstrate that it is possible to obtain water vapour transport rates and diffusion coefficients from an integrated sensor in a glass based packaged OLED structures.

Figure 6:
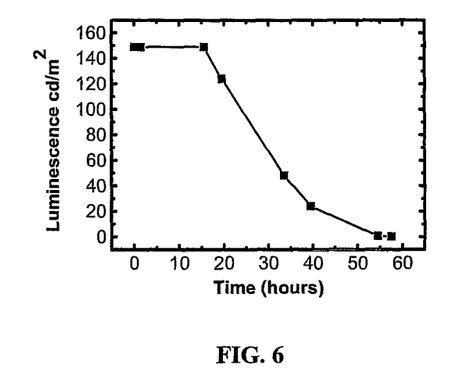
FIG. 6 shows the Luminescence vs. Time graph based on luminescence readings obtained at 5 to 15 hour intervals for an encapsulated OLED with PPV based polymer.

The calcium test structure was integrated with a small molecule (Alq3) and PPV polymer-based OLED device structure fabricated on to the glass substrate using standard processes and encapsulated with a cover glass by rim sealing technique. The purpose of this test is to measure the WVTR properties of this package structure and correlate the results with the lifetime of OLED & PLED with respect to package structure. The devices were kept at a constant temperature of 60° C. and 90% relative humidity. However, the devices were not stressed under constant current or voltage, but 0.5 mA current was applied whenever the luminescence was measured at constant intervals and the results are shown in FIG. 6. This ensures that the devices are stressed only with high temperature and humidity but not electrically. Optical analysis of the calcium sensor was undertaken through a microscope with a CCD camera at intervals.

Figure 7:
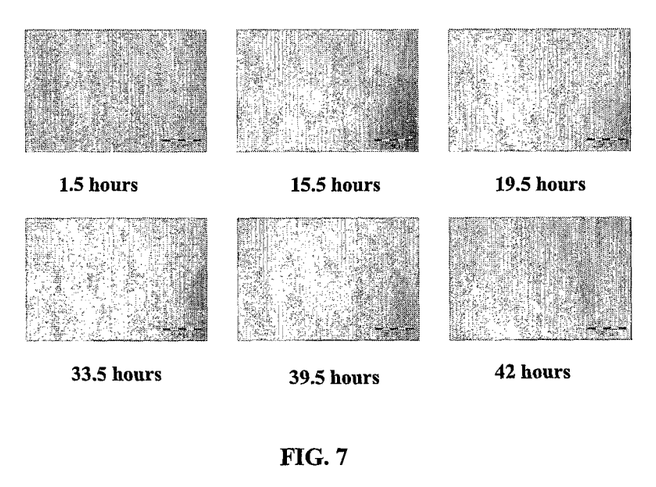
FIG. 7 shows the microscope photographs of the sensing element in the sensor at different time intervals.

It can be seen from the pictures in FIG. 7, a large increase in corroded areas correspond with a large drop in luminance of the OLED device. However, the diode failed before the calcium sensor was fully oxidised. Thus, we can conclude that this measurement methodology can be beneficial in the understanding of device lifetime & degradation phenomena and also useful in estimating water vapor transport properties of the given OLED packages, adhesives and polymer substrates.

Figure 8:
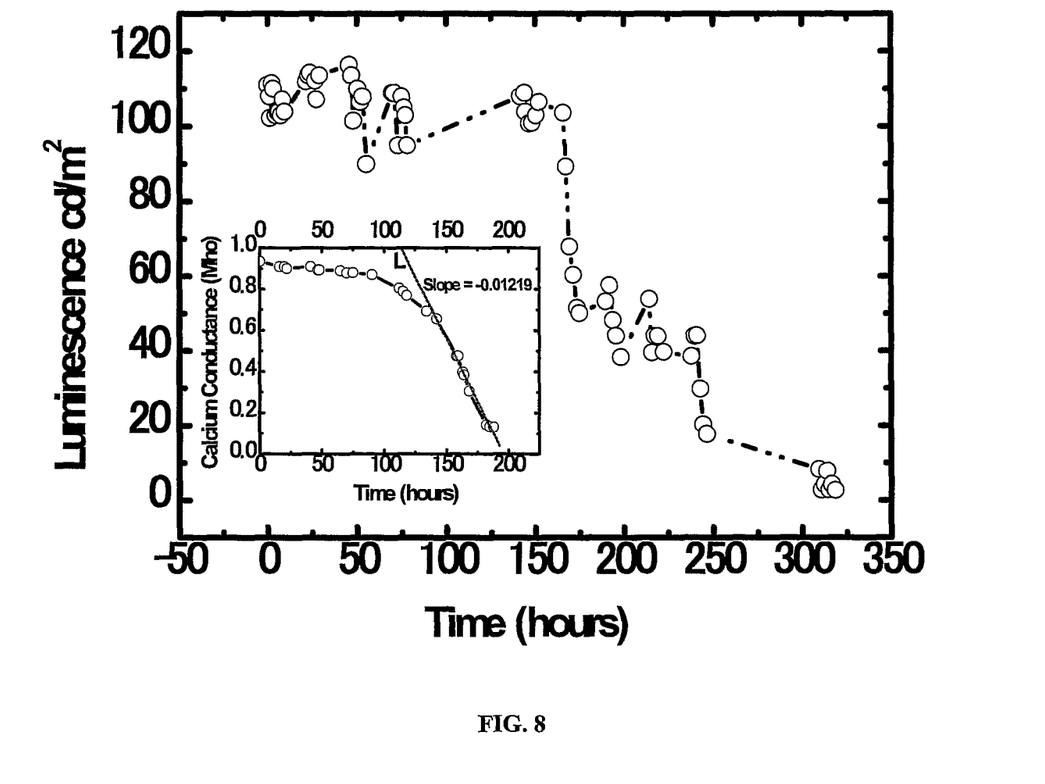
FIG. 8 shows the Luminescence vs. Time and Conductance vs. Time graph of the OLED and the sensor respectively, obtained for an extended period of time over 300 hours.

FIG. 8 shows that the luminescence of the device decreased from 110 cd/m$^2$ to 50 cd/m$^2$ abruptly at 150 hours. The degradation of the device could be due mainly to water vapor permeation through the adhesive sealing, since the device was not electrically stressed. The inset figure shows that the water vapor permeation rate through the 2 mm$^2$ adhesive sealing material into the package is significant and is calculated to be $4.4 \times 10^{-5}$ g/day. From these results, it may be concluded that the measurement method and system would be beneficial for understanding device lifetime and degradation and also useful in estimating water vapor transport properties of the given OLED packages, adhesives and polymer substrates. However, the present vacuum sealed device life-time was shown to longer than 250 hours and calcium test by optical method shown no degradation up to 540 hrs at 60° C. and 90% relative humidity.

Water vapor penetrates through the encapsulation by a solubility diffusion mechanism and gradually permeates enters encapsulation to come into contact with the OLED. Where the sensing element comprises a piece of calcium metal, the desorbed water vapor from the adhesive sealing reacts with the metallic calcium and produces calcium hydroxide [Ca(OH)$_2$] or calcium oxide [CaO]. In addition, the sensing element functions as an electrical resistor, which has optical and electrical properties that change as it gradually reacts with water vapor during the test.

The rate of permeation of water vapor into the package is determined directly by measuring the resistance/conductivity of the sensing element. The plot of conductance against time is shown in FIG. 8 as well. A finite time is required for the water vapor to traverse the barrier, so the desorbing flux is near zero (up to 400 hrs) at the calcium sensor side. The test is carried out in a humidity chamber at a temperature 40° C. and 90% relative humidity. After achieving steady state, the rate of adsorption, the diffusion rate across the barrier, and the rate of de-sorption remains constant and hence, the slope of calcium conductance vs. time remains constant.

Example 3

Integration of Sensors into a Passive Matrix OLED

In this example, the integration of a plurality of sensors into a passive OLED (PMOLED) is demonstrated.

Figure 9:
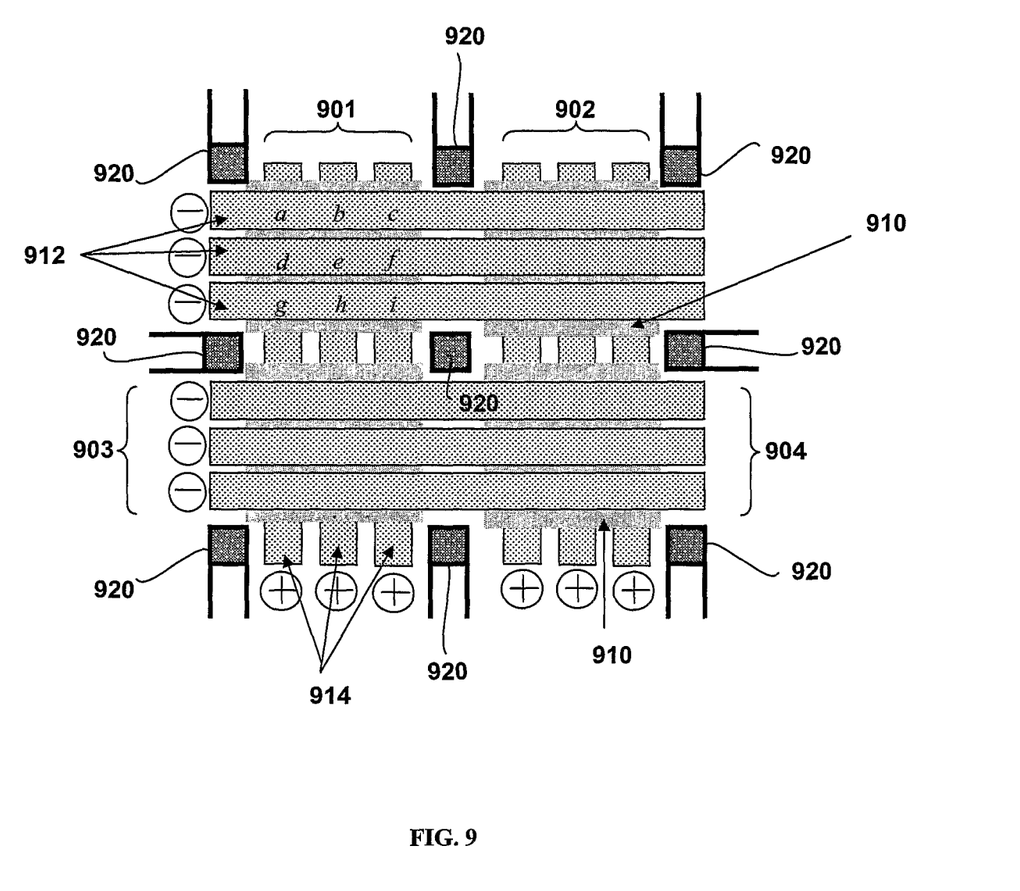
FIG. 9 is a diagrammatic representation of a passive matrix OLED integrated with a plurality of gas permeation sensors.

FIG. 9 shows a diagrammatic representation of a small PMOLED display comprising 4 pixel groups 901, 902, 903, 904. Organic EL layers 910 are arranged between column electrodes 912 (anodes) and row electrodes (914 (cathodes). The anodes are arranged perpendicular to the cathodes, and each intersection of a cathode and anode make up each pixel. In the figure, 9 pixels labelled a to i are comprised in each pixel group. Arranged adjacent to and between each pixel group along the edge of the PMOLED display are gas permeation sensors 920, depicted as dark grey squares.

A drive circuit may be used to provide electrical power to selected strips of anode and cathode, thereby controlling which pixels get turned on and which pixels remain off. The gas permeation sensor may also be coupled to the drive circuit for carrying out gas permeation measurements. As can be seen from this figure, the integration of gas permeation sensors do not require substantial design changes in the architecture of the OLED. In some cases, it may be sufficient for hermeticity measurements to arrange gas permeation sensors along the edge of the encapsulation covering the OLED.

PMOLEDs are most efficient for text and icons and are best suited for small screens (2- to 3-inch diagonal) such as those found in cell phones, PDAs & MP3 players. Even with the external circuitry, PMOLEDs consume less battery power than the LCDs that are currently used in these devices. On the other hand, for more demanding display applications, active matrix OLED (AMOLED) may be used. AMOLEDs have full layers of cathode, organic molecules and anode, but the anode layer overlays a thin film transistor (TFT) array that forms a matrix. The TFT array itself is the circuitry that determines which pixels get turned on to form an image. In general, AMOLEDs consume less power than PMOLEDs because the TFT array requires less power than external circuitry, so they are efficient for large displays. AMOLEDs also have faster refresh rates suitable for video. The best uses for AMOLEDs are computer monitors, large screen TVs and electronic signs or billboards. Gas permeation sensors may be integrated into the architecture of an AMOLED in a similar manner for PMOLEDs as described above.

This invention has been described in terms of illustrative embodiments, and it is to be understood that variations and modifications may be made without departing from the spirit and scope of this invention as set out in the following claims.

What is claimed is:

1. An encapsulated device, comprising
a base substrate,
an electronic component arranged on the base substrate and enclosed within an encapsulation that protects the electronic component from moisture, oxygen, or moisture and oxygen, and
at least one gas permeation sensor arranged on the base substrate and enclosed within the encapsulation, said gas permeation sensor being capable of measuring the permeation of gas into the encapsulation and having at least one physical or physico-chemical property that is at least substantially the same as the electronic component, wherein the at least one physical or physico-chemical property is selected from the group consisting of dimension of an accessible surface of the at least one sensor, surface area-to-volume ratio and reactivity with moisture, oxygen or moisture and oxygen, wherein each of said at least one gas permeation sensor comprises:
an electrically conductive sensing element that is made of a moisture, oxygen, or moisture and oxygen sensitive material, wherein chemical reaction of said material with moisture, oxygen, or moisture and oxygen results in an increase in the electrical resistance of the sensing element,
an electrical connector,
a signal evaluation unit, said signal evaluation unit being coupled to the sensor to measure a property associated with the electrical resistance of the sensor, the electrical connector capable of connecting the sensing element to the signal evaluation unit and a feedback controller, wherein said feedback controller is coupled to the signal evaluation unit to receive feedback therefrom to control the electrical power supplied to the electronic component and wherein the feedback controller increases the electrical power supplied to the electronic component as the extent of gas permeation into the encapsulation increases.

2. The device of claim 1, wherein a plurality of gas permeation sensors are arranged within the encapsulation;
wherein the plurality of gas permeation sensors are arranged in a regular grid around the electronic component; or
wherein the plurality of gas permeation sensors are arranged along the edge of the encapsulation.

3. The device of claim 2, wherein each gas permeation sensor is spaced apart from an adjacent sensor at a distance of at least about 1 cm, or
wherein each of the at least one gas permeation sensor is spaced apart from the electronic component at a distance of between about 1 µm and about 100 µm, or
wherein the gas permeation sensor is arranged at a location within the encapsulation not occupied by the electronic component.

4. The device of claim 1, wherein an electrically insulating material is interposed between the at least one gas permeation sensor and the electronic component, wherein the electrically insulating material is selected from the group consisting of polyimide, parylene, polystyrene, polycarbonate and polyvinyl chloride.

5. The device of claim 1, wherein the sensing element comprises a moisture, oxygen, or moisture and oxygen sensitive material selected from the group consisting of a conductive organic polymer, metal, metal alloy, metal oxide, and mixtures and any combination of the afore-said compounds; and wherein the metal is selected from the group consisting of calcium, iron, magnesium and any combination of the aforesaid compounds; and wherein the conductive organic polymer is selected from the group consisting of polyaniline, polypyrrole and polythiophene, polyacetylene, poly-p-phenylene, and polyvinylpyridine, thiophene-bipyridine copolymers, polypyridine, polybipyridine, organometallic polyphenylenes and any combination of the aforesaid compounds; and wherein the metal oxide is selected from the group consisting of $In_2O_3$, $SnO_2$, $VO_2$, $CrO_2$, $MoO_2$, $LiMn_2O_4$, $Cd_2SnO_4$, $CdIn_2O_4$, $Zn_2SnO_4$ and $ZnSnO_3$, $Zn_2In_2O_5$ and any combination of the aforesaid compounds.

6. The device of claim 1, further comprising a protective layer covering at least a portion of the sensing element of the sensor; and wherein the protective layer comprises a material selected from the group consisting of a metal, a metal alloy, a metal oxide, a metal oxide mixture, a metal nitride, an organic polymer and any combination of the aforesaid compounds.

7. The device of claim 1, further comprising a liner layer applied to at least one surface of the sensing element;

wherein the liner layer is interposed between the sensing element and the base substrate.

8. The device of claim 7, wherein the liner layer comprises an organic polymer that is substantially permeable to gas, and wherein the organic polymer is selected from the group consisting of acrylic polymers, and parylene type polymers (para-xylylene); or wherein the liner layer comprises an inorganic polymer; and wherein the inorganic polymer comprises a silicone-based polymer.

9. The device of claim 1, wherein the electrical connector comprises at least two electrodes, said electrodes extending through the encapsulation, thereby providing exposure for contact with the signal evaluation unit.

10. The device of claim 1, wherein the encapsulation comprises a multilayer film; and wherein the multilayer film comprises at least one barrier layer having low moisture, oxygen, or moisture and oxygen permeability; and wherein the at least one barrier layer comprises a material selected from the group consisting of metals, metal oxides, ceramic oxides, inorganic polymers, organic polymers and mixtures and any combination of the aforesaid compounds; and wherein the organic polymers are selected from the group consisting of an epoxy polymer, polysulfide, silicone and polyurethane.

11. The device of claim 10, wherein the multilayer film comprises at least one layer having distributed therein reactive nanoparticles capable of interacting with moisture, oxygen, or moisture and oxygen to retard the permeation of moisture, oxygen, or moisture and oxygen into the encapsulation.

12. The device of claim 11, wherein the reactive nanoparticles interact with moisture, oxygen, or moisture and oxygen through chemical reaction; and wherein the nanoparticles comprise a material selected from the group consisting of metals, metal oxides and any combination of the aforesaid compounds; and wherein the nanoparticles comprise a metal selected from the group consisting of Al, Ti, Mg, Ba and Ca; and wherein the nanoparticles comprise a metal oxide selected from the group consisting of $TiO_2$, $Al_2O_3$, $ZrO_2$, $ZnO$, $BaO$, $SrO$, $CaO$, $MgO$, $VO_2$, $CrO_2$, $MoO_2$, and $LiMn_2O_4$; and wherein the nanoparticles comprise a transparent conductive oxide selected from the group consisting of cadmium stannate ($Cd_2SnO_4$), cadmium indate ($CdIn_2O_4$), zinc stannate ($Zn_2SnO_4$ and $ZnSnO_3$), and zinc indium oxide ($Zn_2In_2O_5$).

13. The device of claim 11, wherein the reactive nanoparticles interact with moisture, oxygen, or moisture and oxygen through adsorption; and wherein the nanoparticles comprise carbon nanotubes.

14. The device of claim 11, wherein the multilayer film further comprises inert nanoparticles capable of obstructing the permeation of moisture, oxygen, or moisture and oxygen into the encapsulation; and wherein the inert nanoparticles comprise a material selected from the group consisting of gold, copper, silver, platinum, silica, wollastonite, mullite, monmorillonite, silicate glass, fluorosilicate glass, fluoroborosilicate glass, aluminosilicate glass, calcium silicate glass, calcium aluminum silicate glass, calcium aluminum fluorosilicate glass, titanium carbide, zirconium carbide, zirconium nitride, silicon carbide, silicon nitride, metal sulfides, and any combination of the aforesaid compounds.

15. The device of claim 1, wherein the base substrate comprises a polymeric material; and wherein the polymeric material comprises an organic polymer selected from the group consisting of polycarbonate, polyethylene, polythersulfone, epoxy resins, polyethylene terephthalate, polystyrenes, polyurethanes and polyacrylates; or wherein the polymeric material comprises an inorganic polymer selected from the group consisting of silicones, polydimethylsiloxanes, biscyclopentadienyl iron, and polydichlorophosphazene.

16. The device of claim 1, wherein the encapsulation comprises a cover substrate arranged on an adhesive layer surrounding the sensor; and wherein a hollow space is defined within the encapsulation; and wherein the hollow space is filled with an inert gas.

17. The device of claim 16, wherein the cover substrate, the base substrate, or the cover substrate and the base substrate comprises a material selected from the group consisting of glass, indium tin oxide, and transparent plastics.

18. The device of claim 1, wherein the electronic component is coupled to a first drive circuit, and the gas permeation sensor is coupled to a second drive circuit; or wherein the electronic component and the gas permeation sensor are coupled to a common drive circuit.

19. The device of claim 1, further comprising a display unit capable of displaying a quantitative value associated with an amount of moisture, oxygen, or moisture and oxygen that has permeated into the encapsulation.

20. The device of claim 1, wherein the electronic component is selected from the group consisting of an Organic Light Emitting Device (OLED), charged-coupled device (CCD), micro-electro-mechanical sensor (MEMS), organic Thin-Film Transistor (TFT), and a solar cell.

* * * * *